US009241755B2

(12) United States Patent
Jia et al.

(10) Patent No.: US 9,241,755 B2
(45) Date of Patent: Jan. 26, 2016

(54) CAPSULE POLISHING DEVICE AND METHOD FOR CAPSULE POLISHING (75) Inventors: Guangyao Jia, Irvine, CA (US); Glenn R. Sussman, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1114 days.

(21) Appl. No.: 12/777,820

(22) Filed: May 11, 2010

(65) Prior Publication Data

US 2011/0282335 A1    Nov. 17, 2011

(51) Int. Cl.
*A61B 18/14* (2006.01)
*A61B 18/08* (2006.01)
*A61B 18/00* (2006.01)

(52) U.S. Cl.
CPC ..... *A61B 18/082* (2013.01); *A61B 2018/00321* (2013.01); *A61B 2018/141* (2013.01)

(58) Field of Classification Search
CPC .................. A61B 2018/141; A61B 18/082
USPC ............... 606/6, 27–31, 41, 46, 47, 161, 162, 606/166; 607/98, 99, 115; 600/236; 604/113, 114, 294
See application file for complete search history.

(56) References Cited

U.S. PATENT DOCUMENTS

| | | |
|---|---|---|
| 547,867 A | 10/1895 | Taft |
| 560,167 A | 5/1896 | Holmes |
| 974,879 A | 11/1910 | Gwinn |
| 3,159,161 A | 12/1964 | Ness |
| 3,539,034 A | 11/1970 | Woo |
| 3,809,093 A | 5/1974 | Abraham |
| 3,844,272 A | 10/1974 | Banko |
| 3,915,172 A | 10/1975 | Wichterle et al. |
| 3,949,750 A | 4/1976 | Freeman |
| 4,002,169 A | 1/1977 | Cupler, II |
| 4,026,295 A | 5/1977 | Lieberman |

(Continued)

FOREIGN PATENT DOCUMENTS

| | | |
|---|---|---|
| CN | 2501478 Y | 7/2002 |
| DE | 3038024 A1 | 4/1982 |

(Continued)

OTHER PUBLICATIONS

Della, Jaymi E., Office Action Summary, U.S. Appl. No. 12/477,175, Nov. 14, 2011, 39 pages.

(Continued)

*Primary Examiner* — Michael Peffley
*Assistant Examiner* — Thomas Giuliani (57) ABSTRACT Various embodiments of a capsule polishing device include a resistive-heating element including an electrically resistive, superelastic wire forming a loop between first and second ends of the superelastic wire. The first and second ends of the loop may at least partially extend from a planar face defined by the loop, to an insulating portion. In some embodiments, the capsule polishing device may be configured to perform active capsule polishing through a combination of hyperthermia of LECs and mechanical abrasion of the capsule surface. In some embodiments, at least a side and end portion of the loop of the capsule polishing device may be shaped to follow a contour of the capsule bag. The loop may be heated to approximately 40 to 47 degrees Celsius to destroy LECs (other temperatures are also possible). In some embodiments, the loop may include a roughened surface to increase mechanical abrasion.

7 Claims, 9 Drawing Sheets (56) References Cited

U.S. PATENT DOCUMENTS

| | | |
|---|---|---|
| 4,068,664 A | 1/1978 | Sharp et al. |
| 4,210,146 A | 7/1980 | Banko |
| 4,301,802 A | 11/1981 | Poler |
| 4,315,509 A | 2/1982 | Smit |
| 4,367,744 A | 1/1983 | Sole |
| 4,368,734 A | 1/1983 | Banko |
| 4,425,908 A | 1/1984 | Simon |
| 4,457,757 A | 7/1984 | Molteno |
| 4,481,948 A | 11/1984 | Sole |
| 4,485,816 A | 12/1984 | Krumme |
| 4,501,274 A | 2/1985 | Skjaerpe |
| 4,530,356 A | 7/1985 | Helfgott et al. |
| 4,530,359 A | 7/1985 | Helfgott et al. |
| 4,531,934 A | 7/1985 | Kossovsky et al. |
| 4,559,942 A | 12/1985 | Eisenberg |
| 4,570,632 A | 2/1986 | Woods |
| 4,607,622 A | 8/1986 | Fritch et al. |
| 4,616,656 A | 10/1986 | Nicholson et al. |
| 4,665,906 A | 5/1987 | Jervis |
| 4,676,243 A | 6/1987 | Clayman |
| 4,706,669 A | 11/1987 | Schlegel |
| 4,706,671 A | 11/1987 | Weinrib |
| 4,708,138 A | 11/1987 | Pazandak |
| 4,729,761 A | 3/1988 | White |
| 4,766,896 A | 8/1988 | Pao |
| 4,766,897 A | 8/1988 | Smirmaul |
| 4,781,675 A | 11/1988 | White |
| 4,805,616 A | 2/1989 | Pao |
| 4,869,248 A | 9/1989 | Narula |
| 4,869,716 A | 9/1989 | Smirmaul |
| 4,885,004 A | 12/1989 | Pao |
| 4,900,300 A | 2/1990 | Lee |
| 4,911,161 A | 3/1990 | Schechter |
| 4,936,825 A | 6/1990 | Ungerleider |
| 4,950,272 A | 8/1990 | Smirmaul |
| 4,955,859 A | 9/1990 | Zilber |
| 4,955,894 A | 9/1990 | Herman |
| 4,986,825 A | 1/1991 | Bays et al. |
| 4,994,066 A | 2/1991 | Voss |
| 5,047,008 A | 9/1991 | de Juan, Jr. et al. |
| 5,085,664 A | 2/1992 | Bozzo |
| 5,123,906 A | 6/1992 | Kelman |
| 5,135,530 A | 8/1992 | Lehmer |
| 5,180,362 A | 1/1993 | Worst |
| 5,188,634 A | 2/1993 | Hussein et al. |
| 5,199,445 A | 4/1993 | Rubinfeld |
| 5,203,865 A | 4/1993 | Siepser |
| 5,234,436 A | 8/1993 | Eaton et al. |
| 5,242,404 A | 9/1993 | Conley et al. |
| 5,242,449 A | 9/1993 | Zaleski |
| 5,261,923 A | 11/1993 | Soares |
| 5,269,787 A | 12/1993 | Cozean, Jr. et al. |
| 5,322,504 A | 6/1994 | Doherty et al. |
| 5,342,377 A | 8/1994 | Laszerson |
| 5,346,491 A | 9/1994 | Oertli |
| 5,360,399 A | 11/1994 | Stegmann |
| 5,364,405 A | 11/1994 | Zaleski |
| 5,366,443 A | 11/1994 | Eggers et al. |
| 5,374,244 A | 12/1994 | Clement et al. |
| 5,395,361 A | 3/1995 | Fox et al. |
| 5,411,510 A | 5/1995 | Fugo |
| 5,413,574 A | 5/1995 | Fugo |
| 5,423,330 A | 6/1995 | Lee |
| 5,423,841 A | 6/1995 | Kornefeld |
| 5,439,474 A | 8/1995 | Li |
| 5,445,636 A | 8/1995 | Bretton |
| 5,445,637 A | 8/1995 | Bretton |
| 5,455,637 A | 10/1995 | Kallman et al. |
| 5,466,234 A | 11/1995 | Loeb et al. |
| 5,478,338 A | 12/1995 | Reynard |
| 5,484,433 A | 1/1996 | Taylor et al. |
| 5,486,165 A | 1/1996 | Stegmann |
| 5,486,183 A | 1/1996 | Middleman et al. |
| 5,487,725 A | 1/1996 | Peyman |
| 5,509,923 A | 4/1996 | Middleman et al. |
| 5,522,829 A | 6/1996 | Michalos |
| 5,527,332 A | 6/1996 | Clement |
| 5,562,692 A | 10/1996 | Bair |
| 5,569,197 A | 10/1996 | Helmus et al. |
| 5,569,280 A | 10/1996 | Kamerling |
| 5,601,094 A | 2/1997 | Reiss |
| 5,601,572 A | 2/1997 | Middleman et al. |
| 5,601,593 A | 2/1997 | Freitag |
| 5,626,558 A | 5/1997 | Suson |
| 5,630,827 A | 5/1997 | Vijfvinkel |
| 5,632,746 A | 5/1997 | Middleman et al. |
| 5,651,783 A | 7/1997 | Reynard |
| 5,662,670 A | 9/1997 | Michalos |
| 5,669,923 A | 9/1997 | Gordon |
| 5,670,161 A | 9/1997 | Healy et al. |
| 5,683,592 A | 11/1997 | Bartholomew et al. |
| 5,700,243 A | 12/1997 | Narciso, Jr. |
| 5,716,363 A | 2/1998 | Josephberg |
| 5,720,754 A | 2/1998 | Middleman et al. |
| 5,728,117 A | 3/1998 | Lash |
| 5,733,276 A * | 3/1998 | Belkin ............... 606/6 |
| 5,733,297 A | 3/1998 | Wang |
| 5,741,244 A | 4/1998 | Klaas |
| 5,749,879 A | 5/1998 | Middleman et al. |
| 5,755,731 A | 5/1998 | Grinberg |
| 5,766,171 A | 6/1998 | Silvestrini |
| 5,792,166 A | 8/1998 | Gordon et al. |
| 5,820,628 A | 10/1998 | Middleman et al. |
| 5,827,321 A | 10/1998 | Roubin et al. |
| 5,843,019 A | 12/1998 | Eggers et al. |
| 5,860,994 A | 1/1999 | Yaacobi |
| 5,865,800 A | 2/1999 | Mirarchi et al. |
| 5,868,697 A | 2/1999 | Richter et al. |
| 5,873,883 A | 2/1999 | Cozean, Jr. et al. |
| 5,885,279 A * | 3/1999 | Bretton ............... 606/41 |
| 5,888,201 A | 3/1999 | Stinson et al. |
| 5,891,084 A | 4/1999 | Lee |
| 5,893,862 A | 4/1999 | Pratt et al. |
| 5,898,697 A | 4/1999 | Hurme et al. |
| 5,904,690 A | 5/1999 | Middleman et al. |
| 5,911,729 A | 6/1999 | Shikhman et al. |
| 5,921,999 A | 7/1999 | Dileo |
| 5,925,056 A | 7/1999 | Thomas et al. |
| 5,957,921 A | 9/1999 | Mirhashemi et al. |
| 5,989,262 A | 11/1999 | Josephberg |
| 6,004,330 A | 12/1999 | Middleman et al. |
| 6,036,688 A | 3/2000 | Edwards |
| 6,059,792 A | 5/2000 | Josephberg |
| 6,066,138 A * | 5/2000 | Sheffer ............... A61B 18/14 606/107 |
| 6,135,998 A | 10/2000 | Palanker |
| 6,142,996 A | 11/2000 | Mirhashemi et al. |
| 6,162,202 A | 12/2000 | Sicurelli et al. |
| 6,165,190 A | 12/2000 | Nguyen |
| D436,663 S | 1/2001 | Chandler et al. |
| D437,054 S | 1/2001 | Chandler et al. |
| 6,179,830 B1 | 1/2001 | Kokubu |
| D437,413 S | 2/2001 | Chandler et al. |
| 6,203,518 B1 | 3/2001 | Anis et al. |
| 6,217,598 B1 | 4/2001 | Berman et al. |
| 6,241,721 B1 | 6/2001 | Cozean et al. |
| 6,264,668 B1 | 7/2001 | Prywes |
| 6,306,155 B1 | 10/2001 | Chandler et al. |
| 6,379,370 B1 | 4/2002 | Feinsod |
| 6,413,262 B2 | 7/2002 | Saishin et al. |
| 6,440,103 B1 | 8/2002 | Hood et al. |
| 6,447,523 B1 | 9/2002 | Middleman et al. |
| 6,503,263 B2 | 1/2003 | Adams |
| 6,506,176 B1 | 1/2003 | Mittelstein et al. |
| 6,527,766 B1 * | 3/2003 | Bair ............... 606/28 |
| 6,544,254 B1 | 4/2003 | Bath |
| 6,551,326 B1 | 4/2003 | Van Heugten et al. |
| 6,575,929 B2 | 6/2003 | Sussman et al. |
| 6,616,996 B1 | 9/2003 | Keith et al. |
| 6,629,980 B1 | 10/2003 | Eibschitz-Tsimhoni |
| 6,673,064 B1 | 1/2004 | Rentrop |
| 6,764,439 B2 | 7/2004 | Schaaf et al. |
| 6,979,328 B2 | 12/2005 | Baerveldt et al. |
| 6,986,774 B2 | 1/2006 | Middleman et al. |

(56) References Cited

U.S. PATENT DOCUMENTS

| | | |
|---|---|---|
| 7,011,666 B2 | 3/2006 | Feinsod |
| 7,135,009 B2 | 11/2006 | Tu et al. |
| 7,585,295 B2 | 9/2009 | Ben-Nun |
| 7,722,626 B2 | 5/2010 | Middleman et al. |
| 7,785,321 B2 | 8/2010 | Baerveldt et al. |
| 8,128,641 B2 | 3/2012 | Wardle |
| 8,162,931 B2 | 4/2012 | Ben-Nun |
| 8,235,978 B2 | 8/2012 | Ben-Nun |
| 8,323,276 B2 | 12/2012 | Palanker et al. |
| 8,512,321 B2 | 8/2013 | Baerveldt et al. |
| 8,814,854 B2 | 8/2014 | Jia et al. |
| 2001/0044625 A1 | 11/2001 | Hata et al. |
| 2002/0007150 A1 | 1/2002 | Johnson |
| 2002/0049437 A1 | 4/2002 | Silvestrini |
| 2002/0091402 A1 | 7/2002 | Feinsod |
| 2002/0161365 A1 | 10/2002 | Martins |
| 2003/0009177 A1 | 1/2003 | Middleman et al. |
| 2004/0050392 A1 | 3/2004 | Tu et al. |
| 2004/0092982 A1 | 5/2004 | Sheffer |
| 2004/0106929 A1 | 6/2004 | Masket |
| 2004/0116950 A1 | 6/2004 | Eibschitz-Tsimhoni |
| 2004/0220564 A1 | 11/2004 | Ho et al. |
| 2005/0054972 A1 | 3/2005 | Adams et al. |
| 2005/0228419 A1 | 10/2005 | El-Mansoury |
| 2006/0036270 A1 | 2/2006 | Terao |
| 2006/0100617 A1* | 5/2006 | Boukhny .................. 606/41 |
| 2006/0106370 A1 | 5/2006 | Baerveldt et al. |
| 2006/0241580 A1 | 10/2006 | Mittelstein et al. |
| 2006/0259053 A1 | 11/2006 | El-Mansoury |
| 2007/0010812 A1 | 1/2007 | Mittelstein et al. |
| 2007/0049957 A1 | 3/2007 | Benitez |
| 2007/0060926 A1 | 3/2007 | Escaf |
| 2007/0073275 A1 | 3/2007 | Conston et al. |
| 2007/0078359 A1 | 4/2007 | Luloh et al. |
| 2007/0191862 A1 | 8/2007 | Ellis |
| 2007/0239156 A1 | 10/2007 | Palanker et al. |
| 2007/0276420 A1 | 11/2007 | Sorensen et al. |
| 2008/0114341 A1* | 5/2008 | Thyzel .................. 606/11 |
| 2008/0147061 A1* | 6/2008 | Goode et al. .................. 606/45 |
| 2009/0054904 A1 | 2/2009 | Holmen |
| 2009/0137992 A1 | 5/2009 | Nallakrishnan |
| 2009/0216225 A1 | 8/2009 | Ben-Nun |
| 2009/0240149 A1* | 9/2009 | Peyman .................. 600/439 |
| 2009/0287143 A1 | 11/2009 | Line |
| 2009/0287233 A1 | 11/2009 | Huculak |
| 2010/0057069 A1 | 3/2010 | Ben-Nun |
| 2010/0094278 A1* | 4/2010 | Jia et al. .................. 606/41 |
| 2010/0106155 A1 | 4/2010 | Anderson et al. |
| 2010/0145331 A1 | 6/2010 | Chrisitian et al. |
| 2010/0145447 A1 | 6/2010 | Jia et al. |
| 2010/0179544 A1 | 7/2010 | Boukhny et al. |
| 2010/0274272 A1 | 10/2010 | Medina |
| 2010/0298820 A1 | 11/2010 | Ben-Nun |
| 2010/0312252 A1* | 12/2010 | Jia et al. .................. 606/107 |
| 2011/0054384 A1* | 3/2011 | Brown .................. 604/22 |
| 2011/0087256 A1 | 4/2011 | Wiener et al. |
| 2011/0202049 A1 | 8/2011 | Jia et al. |
| 2012/0158027 A1 | 6/2012 | Moradian et al. |
| 2012/0158130 A1 | 6/2012 | Moradian et al. |
| 2013/0066351 A1 | 3/2013 | Giardina et al. |
| 2013/0158573 A1 | 6/2013 | Zaidman et al. |
| 2013/0197548 A1 | 8/2013 | Keller |
| 2013/0289545 A1 | 10/2013 | Baerveldt et al. |

FOREIGN PATENT DOCUMENTS

| | | |
|---|---|---|
| DE | 3205959 A1 | 9/1983 |
| DE | 3248101 A1 | 6/1984 |
| DE | 3434930 A1 | 4/1986 |
| DE | 8710541 U1 | 11/1987 |
| DE | 197 40 530 A1 | 3/1990 |
| DE | 4012882 A1 | 10/1991 |
| DE | 9311879 U1 | 11/1993 |
| DE | 19719549 A1 | 11/1998 |
| DE | 19809510 A1 | 9/1999 |
| DE | 10220253 A1 | 11/2002 |
| EP | 0170650 B1 | 8/1985 |
| EP | 183385 B1 | 3/1989 |
| EP | 165657 B1 | 7/1989 |
| EP | 0335714 A2 | 10/1989 |
| EP | 358990 A1 | 3/1990 |
| EP | 0228185 B1 | 7/1990 |
| EP | 0355341 B1 | 10/1992 |
| EP | 0537116 A1 | 4/1993 |
| EP | 506618 B1 | 7/1995 |
| EP | 0730848 A2 | 9/1996 |
| EP | 0730848 A3 | 7/1997 |
| EP | 0788802 A2 | 8/1997 |
| EP | 0898947 A2 | 3/1999 |
| EP | 0730848 B1 | 4/2000 |
| EP | 0788802 A3 | 4/2000 |
| EP | 1010410 A1 | 6/2000 |
| EP | 1027906 A2 | 8/2000 |
| EP | 0986328 A4 | 5/2001 |
| EP | 1095641 A1 | 5/2001 |
| EP | 0788802 B1 | 7/2006 |
| EP | 1809196 A4 | 3/2008 |
| EP | 1809196 B1 | 9/2010 |
| EP | 1871216 B1 | 6/2012 |
| ES | 2 103 635 | 9/1997 |
| FR | 2544979 A1 | 11/1984 |
| FR | 2588751 A1 | 4/1987 |
| FR | 2 676 355 | 11/1992 |
| FR | 2677244 A1 | 12/1992 |
| FR | 2702955 A1 | 9/1994 |
| FR | 2707872 A1 | 1/1995 |
| FR | 2830186 A1 | 4/2003 |
| FR | 2855745 A1 | 12/2004 |
| FR | 2855746 A1 | 12/2004 |
| FR | 2924924 A1 | 6/2009 |
| GB | 2247174 A | 2/1992 |
| GB | 2437252 A | 10/2007 |
| JP | 2004-523272 | 8/2004 |
| JP | 2007014510 | 1/2007 |
| JP | 2007-83049 | 4/2007 |
| JP | 2008-538306 A | 10/2008 |
| KR | 20100016724 | 2/2010 |
| KR | 20100121583 | 11/2010 |
| KR | 101039394 B1 | 6/2011 |
| KR | 101039398 81 | 6/2011 |
| RU | 1766403 A1 | 10/1992 |
| RU | 1790934 A1 | 1/1993 |
| RU | 1790935 A1 | 1/1993 |
| RU | 1148613 A1 | 4/1995 |
| RU | 2238710 C1 | 10/2004 |
| SU | 452338 | 12/1974 |
| SU | 1301400 A1 | 4/1987 |
| SU | 1395314 A1 | 5/1988 |
| SU | 1431752 A1 | 10/1988 |
| SU | 1440496 A1 | 11/1988 |
| WO | WO 86/02257 A1 | 4/1986 |
| WO | WO 93/01755 A1 | 2/1993 |
| WO | WO 93/20765 A1 | 10/1993 |
| WO | WO 95/08310 A1 | 3/1995 |
| WO | WO 96/06570 A1 | 3/1996 |
| WO | WO 97/26835 A1 | 7/1997 |
| WO | WO 97/30669 A1 | 8/1997 |
| WO | WO 98/49945 A1 | 11/1998 |
| WO | WO 99/60936 A1 | 12/1999 |
| WO | WO 00/48540 A1 | 8/2000 |
| WO | WO 01/56519 A1 | 8/2001 |
| WO | WO 01/60266 A1 | 8/2001 |
| WO | WO 03/022174 A2 | 3/2003 |
| WO | WO 03/022174 A3 | 3/2003 |
| WO | WO 03/039335 A2 | 5/2003 |
| WO | WO 03/039335 A3 | 5/2003 |
| WO | WO 03/045290 A1 | 6/2003 |
| WO | WO 2004/039295 A1 | 5/2004 |
| WO | WO 2004/071312 A1 | 8/2004 |
| WO | WO 2006/052374 A2 | 5/2006 |
| WO | WO 2006/052374 A3 | 5/2006 |
| WO | WO 2006/109255 A1 | 10/2006 |
| WO | WO 2006/109290 A2 | 10/2006 |

(56) References Cited

FOREIGN PATENT DOCUMENTS

| | | |
|---|---|---|
| WO | WO 2006/117772 A1 | 11/2006 |
| WO | WO 2007/121485 A2 | 10/2007 |
| WO | WO 2008/080149 A1 | 7/2008 |
| WO | 2008/115455 | 9/2008 |
| WO | WO 2009/140414 A1 | 11/2009 |
| WO | WO 2009/153550 A1 | 12/2009 |
| WO | WO 2010/044988 A1 | 4/2010 |
| WO | WO 2010/068662 A1 | 6/2010 |
| WO | WO 2010/141179 A1 | 12/2010 |
| WO | WO 2010/141181 A1 | 12/2010 |
| WO | WO 2011/102928 A1 | 8/2011 |
| WO | 2013/022854 A1 | 2/2013 |
| WO | 2013/070423 A1 | 5/2013 |
| WO | 2013/073609 A1 | 5/2013 |

OTHER PUBLICATIONS

Della, Jaymi E., Office Action Summary, U.S. Appl. No. 12/477,175, Feb. 28, 2012, 12 pages.
Abstract of JP4834337(B2); Publication date Dec. 14, 2011.
International Searching Authority, International Search Report, International Application No. PCT/US2010/033893, Jul. 8, 2010, 5 pages.
International Searching Authority, Written Opinion of the International Searching Authority, International Application No. PCT/US2010/033893, Jul. 8, 2010, 8 pages.
International Searching Authority, International Preliminary Report on Patentability, International Application No. PCT/US2009/057836, Apr. 19, 2011, 7 pages.
International Searching Authority, Written Opinion of the International Searching Authority, International Application No. PCT/US2009/057836, Apr. 19, 2011, 6 pages.
International Searching Authority, International Search Report, International Application No. PCT/US2010/033949, Jul. 23, 2010, 6 pages.
International Searching Authority, Written Opinion of the International Searching Authority, International Application No. PCT/US2010/033949, Jul. 23, 2010, 9 pages.
International Searching Authority, International Search Report, International Application No. PCT/US2011/021608, Mar. 1, 2011, 6 pages.
International Searching Authority, Written Opinion of the International Searching Authority, International Application No. PCT/US2011/021608, Mar. 1, 2011, 9 pages.
Holloway, Ian Knobel, Office Action Summary, U.S. Appl. No. 12/249,982, May 11, 2011, 23 pages.
Della, Jaymi E., Office Action Summary, U.S. Appl. No. 12/477,175, Jun. 18, 2012, 12 pages.
Holloway, Ian Knobel, Office Action Summary, U.S. Appl. No. 12/249,982, Jun. 18, 2012, 7 pages.
Fowler, Daniel Wayne, Office Action Summary, U.S. Appl. No. 12/707,747, Aug. 31, 2012, 34 pages.
Bretton, Randolph H. et al., "Use of bipolar diathermy to prevent posterior capsule opacification," Journal of Cataract Refractive Surgery 2002; 2 8:866-878.
Sussman, Glen et al., Capsularhexis Device with Flexible Heating Element having an Angled Transitional Neck, U.S. Appl. No. 12/477,175, filed Jun. 3, 2009, 32 pages.
International Searching Authority, International Preliminary Report on Patentability, PCT/US2005/036670, May 15, 2007, 4 pages.
Huculak, John C. et al., Capsularhexis Device Using Pulsed Electric Fields, U.S. Appl. No. 12/618,805, filed Nov. 16, 2009, 14 pages.
Jia, Guangyao, et al., Capsulotomy Repair Device and Method for Capsulotomy Repair, U.S. Appl. No. 12/754,119, filed Apr. 5, 2010, 40 pages.
Sussman, Glenn, et al., Small Gauge Ablation Probe for Glaucoma Surgery, U.S. Appl. No. 12/707,747, filed Feb. 18, 2010, 11 pages.
Lewandowski, Julia T., "Improving Ab Interno Trabeculotomy, A combination of advanced technology and insightful design may prompt surgeons to adopt a new technique for lowering IOP," article, Jul. 2007, 4 pages, Bryn Mawr Communications.
Abstract of SU1805938; Publication date Mar. 30, 1993; Priority date Mar. 11, 1991.
Karmel, Miriam, "Glaucoma Surgies: Trabectome and Canaloplasty Take the Stage," publication, May 2009, pp. 29-30, American Academy of Ophthalmology.
Holloway, Ian Knobel, Office Action Summary, U.S. Appl. No. 12/249,982, Jan. 3, 2014, 9 pages.
Stigell, Theodore J., Office Action Summary, U.S. Appl. No. 12/249,982, Dec. 19, 2014, 51 pages.
Della, Jaymi E., Office Action Summary, U.S. Appl. No. 12/477,175, Aug. 15, 2014, 36 pages.
Della, Jaymi E., Office Action Summary, U.S. Appl. No. 12/477,175, Nov. 17, 2014, 20 pages.
Stigell, Theodore J., Office Action Summary, U.S. Appl. No. 12/249,982, Mar. 4, 2015, 7 pages.

* cited by examiner

CAPSULE POLISHING DEVICE AND METHOD FOR CAPSULE POLISHING

FIELD OF THE INVENTION

The present invention relates generally to the field of ophthalmic surgery and more particularly to methods and apparatus for capsule polishing.

DESCRIPTION OF THE RELATED ART

An accepted treatment for the treatment of cataracts is surgical removal of the lens (e.g., through phacoemulsification) and replacement of the lens function by an artificial intraocular lens (IOL). After phacoemulsification, there is a risk of posterior capsule opacification (PCO) caused by a build-up of lens epithelial cells which may inhibit vision and/or dislocate the IOL.

SUMMARY OF THE INVENTION

Various embodiments of a capsule polishing device include a resistive-heating element including an electrically resistive, superelastic wire forming a loop between first and second ends of the superelastic wire. The first and second ends of the loop may at least partially extend from a planar face defined by the loop, to an insulating portion. In some embodiments, the capsule polishing device may be configured to perform active capsule polishing through a combination of hyperthermia of LECs and mechanical abrasion of the capsule surface. In some embodiments, at least a side and end portion of the loop of the capsule polishing device may be shaped to follow a contour of the capsule bag. The loop may be heated to approximately 40 to 47 degrees Celsius to destroy LECs (other temperatures are also possible). In some embodiments, the loop may include a roughened surface to increase mechanical abrasion.

BRIEF DESCRIPTION OF THE DRAWINGS

For a more complete understanding of the present invention, reference is made to the following description taken in conjunction with the accompanying drawings in which.

It is to be understood that both the foregoing general description and the following detailed description are exemplary and explanatory only and are intended to provide a further explanation of the present invention as claimed.

DETAILED DESCRIPTION OF THE EMBODIMENTS

Incorporation by Reference

U.S. patent application Publication entitled "CAPSULARHEXIS DEVICE," Publication No. 20060100617, Ser. No. 10/984,383, by Mikhail Boukhny filed Nov. 9, 2004 is hereby incorporated by reference in its entirety as though fully and completely set forth herein.

U.S. patent application entitled "CAPSULARHEXIS DEVICE WITH FLEXIBLE HEATING ELEMENT," Ser. No. 12/249,982, by Glenn Sussman and Guangyao Jia filed Oct. 13, 2008 is hereby incorporated by reference in its entirety as though fully and completely set forth herein.

U.S. patent application entitled "CAPSULARHEXIS DEVICE WITH FLEXIBLE HEATING ELEMENT HAVING AN ANGLED TRANSITIONAL NECK," Ser. No. 12/477,175, by Guangyao Jia and Glenn R. Sussman filed Jun. 3, 2009 is hereby incorporated by reference in its entirety as though fully and completely set forth herein.

Figure 1:
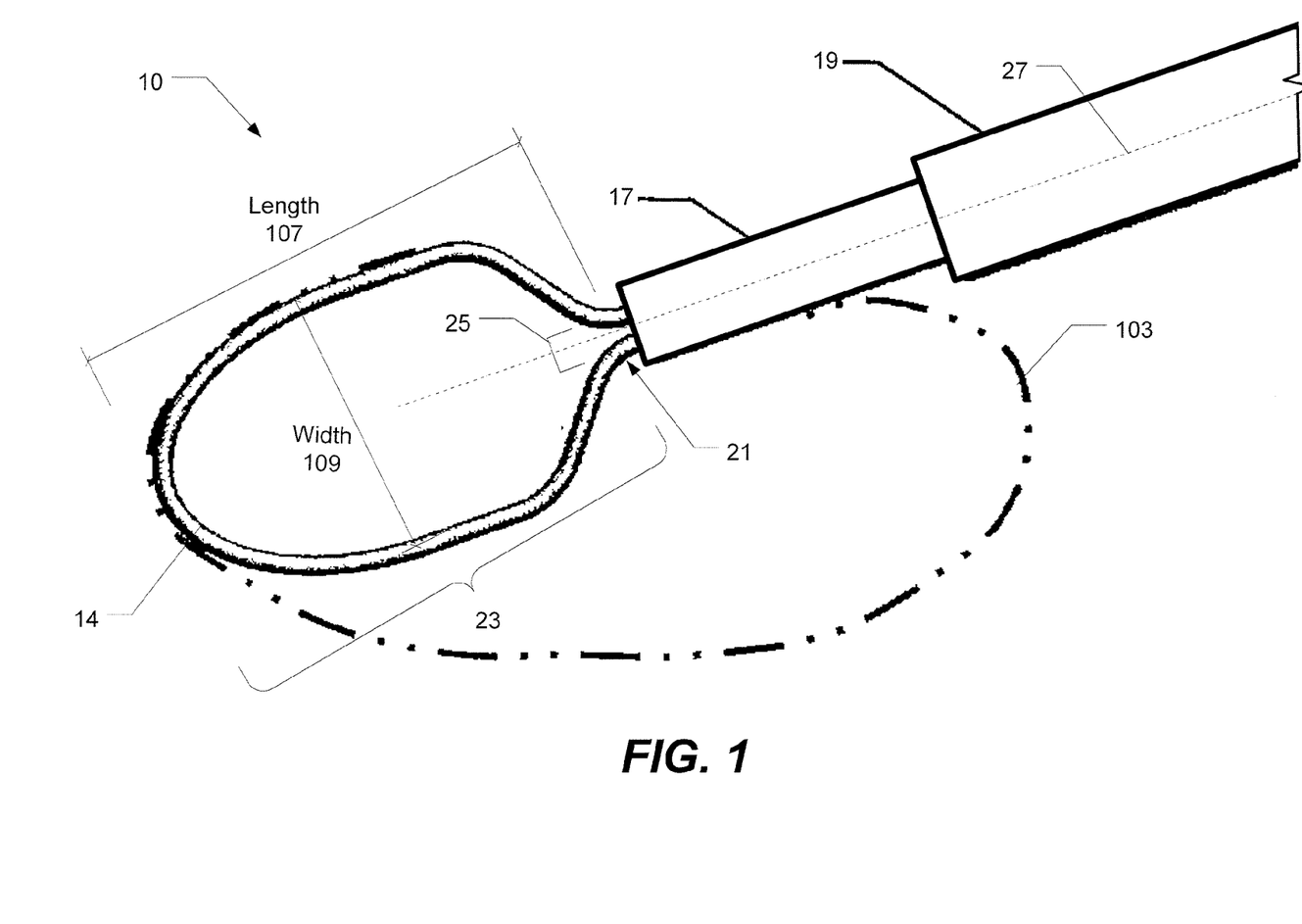
FIG. 1 illustrates a capsule polishing device, according to an embodiment.

FIG. 1 shows a plan view of some embodiments of a capsule polishing device 10. Those skilled in the art will appreciate that FIG. 1, like the several other attached figures, are not to scale, and that several of the features may be exaggerated to more clearly illustrate various features. Those skilled in the art will also appreciate that the illustrated structures are only exemplary, and not limiting. In some embodiments, the capsule polishing device 10 may be used for active capsule polishing. In some embodiments, the capsule polishing device 10 may be used to destroy and/or remove lens epithelial cells (LECs) on the capsule after phacoemulsification (e.g., to prevent incidence of posterior capsule opacification (PCO)). In some embodiments, the capsule polishing device 10 may perform active capsule polishing through a combination of hyperthermia of LECs and mechanical abrasion of the capsule surface (without puncturing the capsule surface). As shown in FIG. 1, in some embodiments, the capsule polishing device 10 may include a wire 14 (e.g., shaped in a wire loop 23), a handle/insulating portion 17 to hold the loop 23, and an insertion sleeve 19 for intraocular manipulation.

In some embodiments, the loop 23 may be electrically interfaced with a radio-frequency (RF) power unit for elevation of loop temperature by resistance heating. The size and shape of the loop 23 may be designed to provide a contour that fits the capsule bag so that sufficient contact may be established between the loop 23 and the capsule surface, as illustrated in FIG. 1. For example, a side and the front of loop 23 may be shaped to fit the contour 103 of a cross section of the capsule bag. As shown in FIG. 1, the length 107 and width 109 of the loop 23 may be less than approximately 10 mm (e.g., a length approximately in a range of 4 to 5 mm and a width approximately in a range of 2.5 to 3.5 mm). Other lengths and widths are also possible. In some embodiments, the loop 23 may have an irregular configuration (e.g., with non-oval portions) to better fit the contour 103. Other shapes of the loop 23 are also contemplated (e.g., circular, rectangular, irregular, etc). By heating the loop 23 to a temperature, for example, between 40 to 47 degrees Celsius (e.g., between 42 degrees Celsius and 45 degrees Celsius) and rubbing it against the capsule surface, LECs may be destroyed and/or removed from the capsule as a result of: (1) hyperthermia that may cause death of LECs, swelling of the cytoplasm and decreased cell adhesion to the capsule surface, and (2) mechanical abrasion. Other temperature ranges may also be used (e.g., 30-42 degrees C. or 45-60 degrees C.). In some embodiments, a configuration of the capsule polishing device 10 (e.g., the small wire diameter and high abrasion surface) may achieve destruction/removal of the LECs with a small magnitude of force.

Figure 3A:
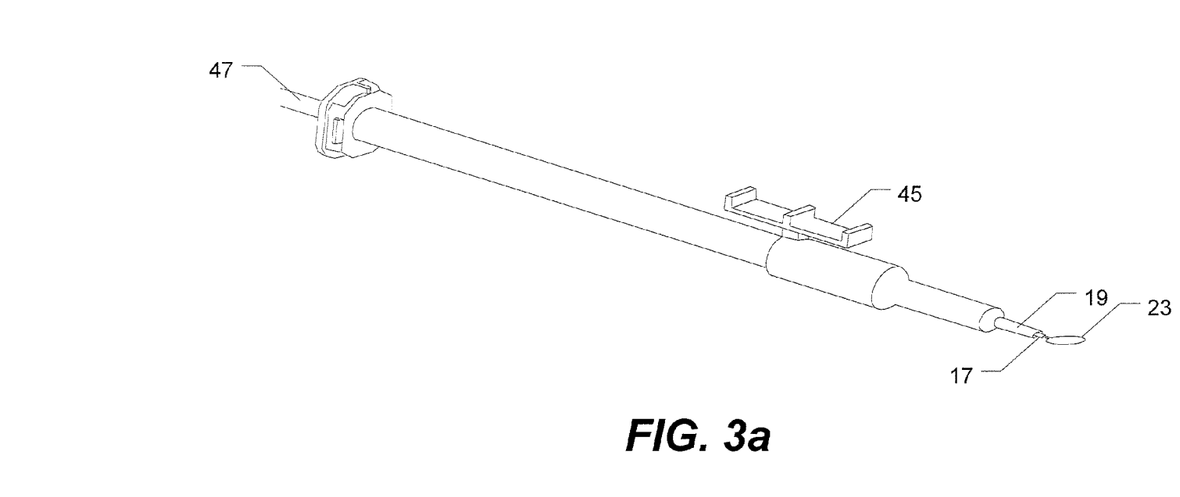
FIGS. 3a-b illustrate an embodiment of the handpiece.
Figure 3B:
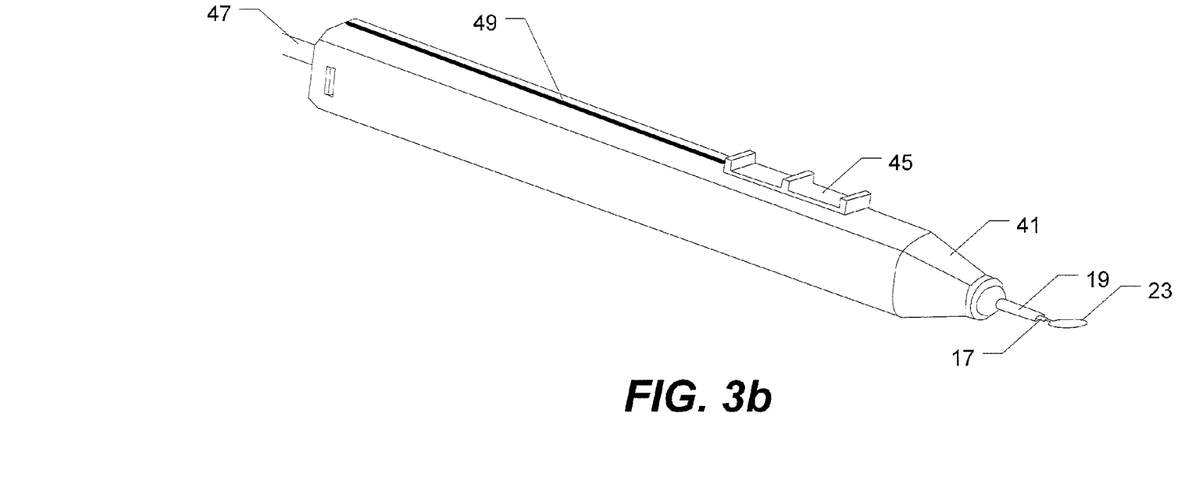

In some embodiments, the loop 23 may be formed of a shape memory element (such as superelastic Nitinol) to be collapsible upon retracting it into the insertion sleeve 19/hand piece 41 and expandable to its original shape upon extending it out from the tip of the insertion sleeve 19/hand piece 41 (e.g., see FIGS. 3*a-b*). Other materials are also possible (e.g., stainless steel, titanium alloy, etc). In some embodiments, the loop 23 may include a roughened surface or applied abrasive to increase the mechanical abrasion characteristics of the loop 23.

As seen in FIG. 1, in various embodiments, the wire 14 may include a straight neck 21 with a planar face of the loop 23 generally in line with a centerline 27 of an insertion sleeve 19. In some embodiments, the wire ends forming neck 21 may bend away from the centerline 27 (to offset the planar face of the loop 23 from the centerline 27). Bending away from the centerline 27 may allow the loop 23 to be placed more parallel with an anterior and/or posterior capsule face. In some embodiments, the length 107/width 109 of the loop 23 may be adjusted according to whether the loop 23 will be used in the anterior or posterior lens portion (e.g., the loop may have larger dimensions for use in the anterior portion). In some embodiments, the straight neck 21 may have a length (a distance from the insulating portion 17 to the loop 23) of approximately 1-2 mm (other lengths are also contemplated).

In some embodiments, the straight neck 21 may be substantially (e.g., +/−20 degrees) in line with the planer face of the loop 23. Other configurations are also contemplated. In some embodiments, the wire ends may be bent toward each other to reduce the size of gap 25 between the wire ends of the loop 23. The gap 25 between the wire ends may be reduced but maintain enough distance to prevent a short between ends of the gap 25 (i.e., so current travels around the loop 23). For example, the gap 25 may have a width of approximately 0.003 inches plus or minus 0.001 inches. Other dimensions are also contemplated (e.g., 0.006 inches or, as another example, smaller than 0.002 inches). The gap 25 may insulate the wire ends from each other (such that electric current travels through wire 14 and not across gap 25). Bending away from the centerline 27 may allow a further reduction in the size of gap 25 than would be otherwise possible if the wire ends 31 were parallel to the centerline 27. Wire ends may be curved and/or straight. Other configurations for the wire ends are also contemplated. While the term "bending" is used throughout, the wire ends may be formed and/or shaped using other methods (e.g., mold casting, extrusion, etc).

According to several embodiments, the resistive-heating wire 14 may include an at least partially bare resistance-heating element made from a super-elastic wire. By combining the super-elasticity of the wire material with a relatively high electric resistivity, a collapsible, ring-shaped heating wire 14 may be constructed to perform capsule polishing by localized heating. Because the heating wire 14 may be collapsible, the heating wire 14 may be easily inserted into the eye 32 through a small incision 505 (e.g., 2 mm) in the cornea 511 (e.g., see FIG. 6). Other incision sizes and locations are also contemplated.

The capsule polishing device 10 may include a fine, super-elastic wire 14. In some embodiments, the wire 14 may be formed from a nickel titanium alloy, such as Nitinol, which may exhibit superelastic and shape memory properties. Because the wire 14 may be superelastic (which term is intended herein as a synonym for the somewhat more technically precise term "pseudoelastic"), the wire 14 may be able to withstand a significant amount of deformation when a load is applied and return to its original shape when the load is removed. (Those skilled in the art will appreciate that this property is distinct from, although related to, "shape memory", which refers to a property exhibited by some materials in which an object that is deformed while below the material's transformation temperature returns to its former shape when warmed to above the transformation temperature. Nitinol exhibits both properties; superelasticity is exhibited above the transformation temperature.) Further, Nitinol is resistive, and can thus be heated with an electrical current, making it useful for forming the resistive-heating wire 14. Of course, those skilled in the art will appreciate that other materials that are resistive and superelastic may be used instead of Nitinol in some embodiments. In some embodiments, the wire 14 may not be elastic (e.g., the wire 14 may be fixed/rigid).

Because the wire 14 may have superelastic properties, the wire 14 may be able to collapse during insertion and return to a pre-formed shape during use. In some embodiments, a viscoelastic agent may be used to inflate the anterior chamber 34 prior to the capsule polishing. The viscoelastic agent may have a sufficiently low thermal diffusivity to serve as a thermal insulator around the heating wire 14, thus facilitating the formation of a highly concentrated thermally affected zone in the immediate vicinity of the heating wire 14. The concentration of this zone may reduce collateral damage to nearby tissue. Although in practice it may be unavoidable to trap a thin film of viscoelastic material between the heating element and the capsule, a small defined area on the capsule 36 may still respond sufficiently fast to the temperature rise in the heating element to avoid collateral damage, due to the small thickness (e.g., approximately 10 micrometers) of the fluid film.

In some embodiments, the ends of the wire 14, extending away from the loop 23 to form a lead section, may be kept electrically separate with a flexible, electrically insulating portion 17. In some embodiments, the insulating portion 17 may surround a portion of the lead section. However, those skilled in the art will appreciate that insulating portion 17 may surround only one lead, or may only partially surround either or both leads, in some embodiments, provided that the two leads extending away from the loop 23 and into the insertion sleeve 19 may be kept electrically separate so that electrical current may be passed through the loop 23 of the resistive-heating wire 14. Insulating portion 17 may include a biocompatible and high temperature-resistant material, such as polyimide or Teflon™. In some embodiments, insulating portion 17 may be flexible. In some embodiments, one or more crimp tubes (e.g., silver crimp tubes) may be used to receive the loop 23 (the tubes may be crimped onto the loop 23 to secure the loop 23 into the handpiece). In some embodiments, insulating portion 17 may extend over the crimp tubes to electrically insulate the tubes from each other.

In some embodiments, insertion sleeve 19 may include a flat or cylindrical tube that engages a portion of a lead section, including the insulating portion 17. In some embodiments, the insertion sleeve 19 may form a slip-fit with the insulating portion 17. Insertion sleeve 19 may be used to insert the heating wire 14 into the eye 32 during the capsule polishing procedure and to retract the heating wire 14 afterwards. The insertion sleeve 19, which may be made from a thermoplastic, may also contain electrical connectors and/or connecting wires so that the heating wire 14 may be selectively connected to a power source for heating. In some embodiments, the insertion sleeve 19, insulation material 17, and wire 14 may form a disposable unit that can be selectively connected during use to a handpiece or other apparatus that can supply electrical current. In some embodiments, insertion sleeve 19 may be coupled to handpiece 41 which may be coupled to a surgical console 43 (e.g., see FIG. 9).

Figure 2:
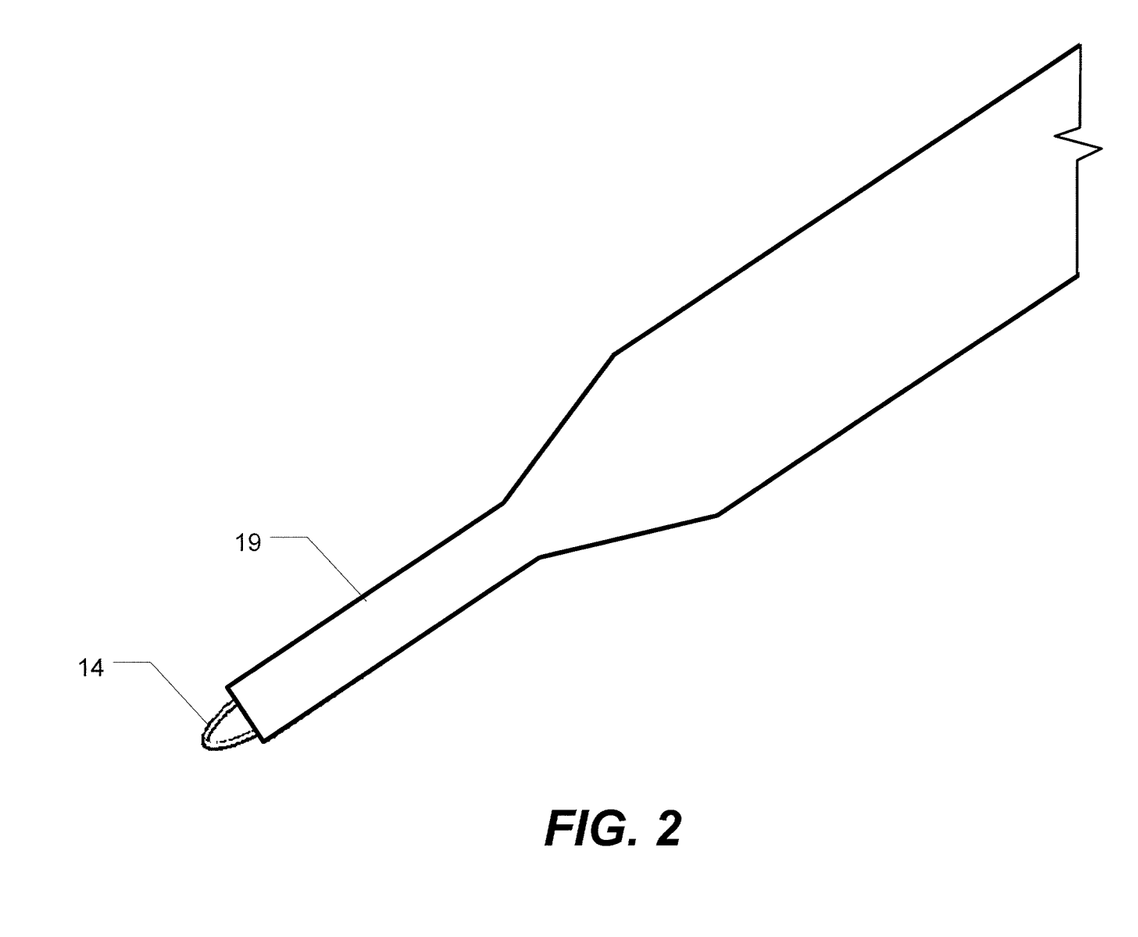
FIG. 2 illustrates a withdrawn capsule polishing device, according to an embodiment.
Figure 4A:
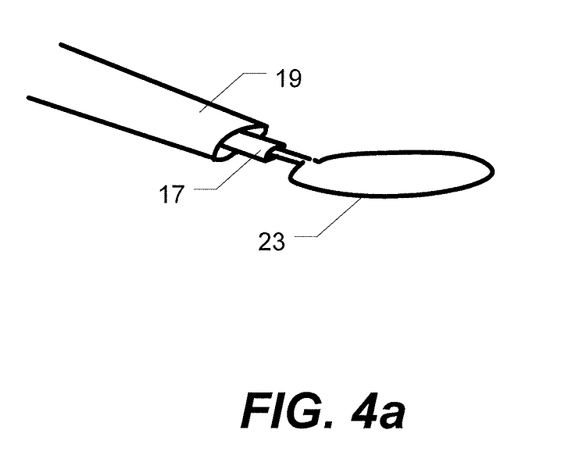
FIGS. 4a-b illustrate an embodiment of an exposed loop and a withdrawn loop.
Figure 6:
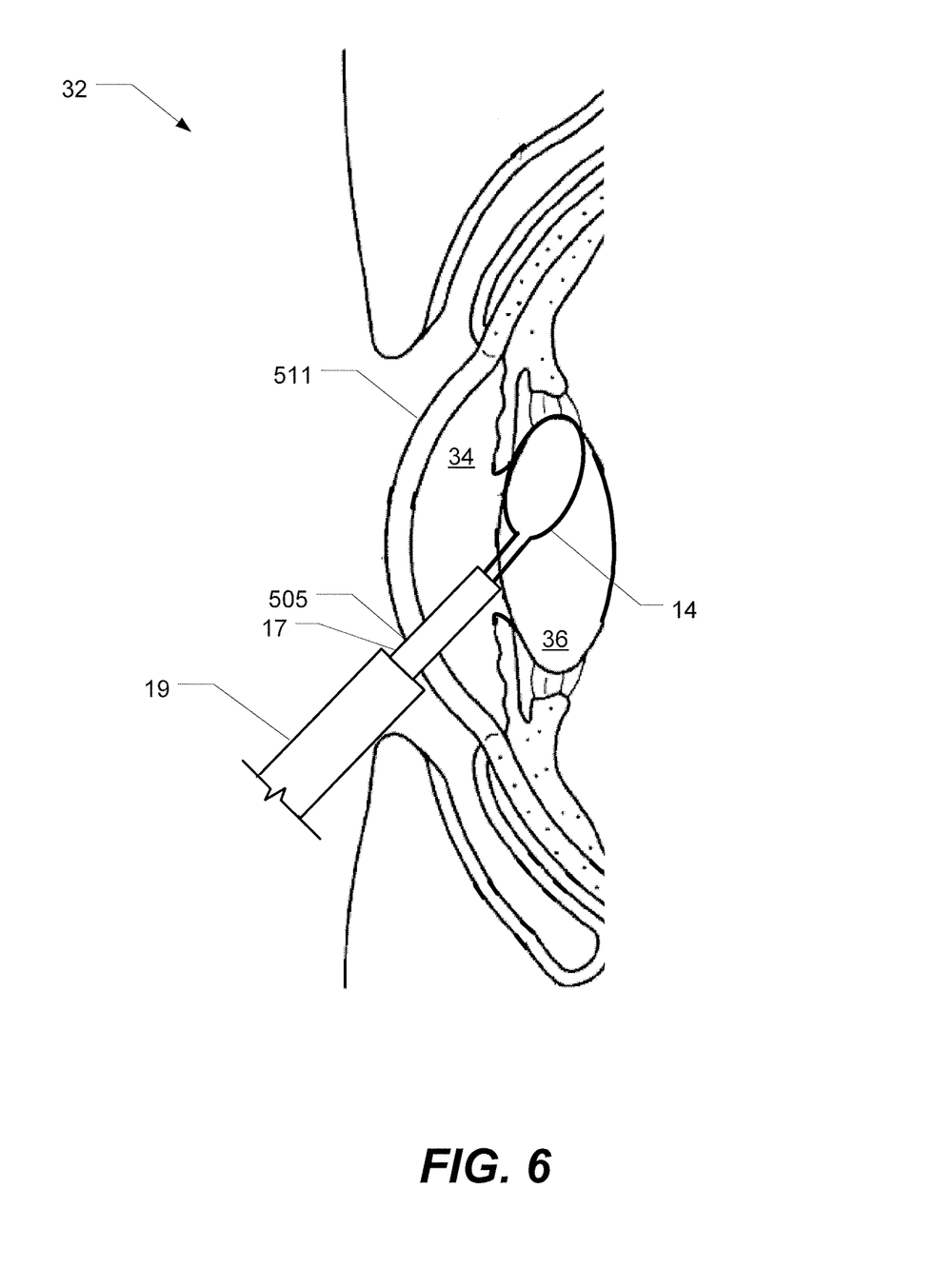
FIG. 6 illustrates a side view of the capsule polishing device inserted into the posterior capsule, according to an embodiment.

As seen in FIG. 6, because of its superelastic properties, the heating wire 14 may be collapsed for insertion into the anterior chamber 34 of the eye 32, regaining its pre-defined shape within the anterior chamber 34. Accordingly, some embodiments include or may be used with an insertion sleeve 19 through which the heating wire 14 is pushed. The heating wire 14 may be collapsible upon retracting the heating wire 14 into the insertion sleeve 19 and expandable to its original shape upon ejection from the insertion sleeve 19. In some embodiments, the insertion sleeve 19 and insulating portion 17 may be incorporated in a single device (or separate devices). In some embodiments, a separate cartridge may be used to collapse/expand the loop 23 through (e.g., separate from and/or in place of insertion sleeve 19). As seen in FIGS. 3*a-b*, a handpiece 41 may include a retraction lever 45 which may ride in a slot 49. When retraction lever 45 (attached to the insertion sleeve) is pushed towards the end of the slot 49, the loop 23 may be enclosed in the insertion sleeve 19 (e.g., see FIG. 4*b*). When the retraction lever 45 is pulled back along the slot 49, the loop 23 may exit the insertion sleeve 19 (see FIG. 4*a*). In some embodiments, power may be supplied to the hand piece 41 through cable 47 (e.g., from surgical console 43). Other configurations of the handpiece are also contemplated. In various embodiments, the loop 23 may be partially withdrawn into the insertion sleeve 19 (e.g., see FIG. 2) or fully withdrawn into the insertion sleeve 19 (e.g., see FIG. 4*b*) before and/or after the procedure. As seen in FIG. 2, the partially exposed wire may act as a guide as the insertion sleeve 19 is inserted into an incision.

Figure 5A:
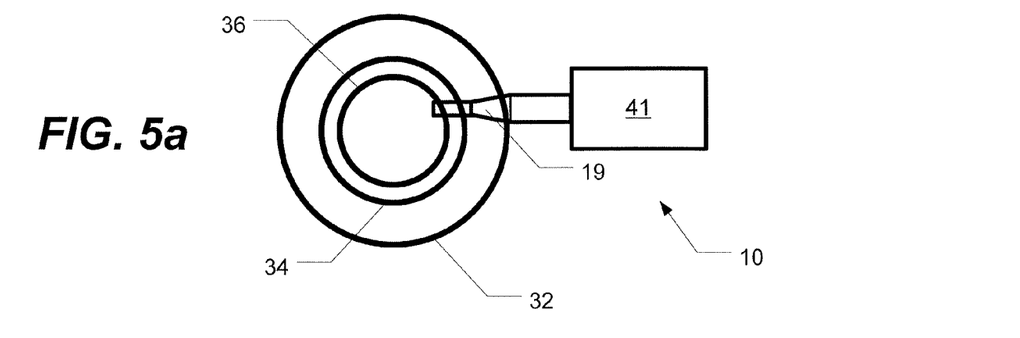
FIGS. 5a-d illustrate expansion and retraction of the capsule polishing device through an insertion sleeve, according to an embodiment.

FIGS. 5*a-d* illustrate the insertion of the heating wire 14 into an eye 32, according to an embodiment. Prior to the procedure, the loop 23 of the heating wire 14 may be withdrawn into the insertion sleeve 19, so that, as seen in FIG. 5*a*, the loop 23 of heating wire 14 is contained almost entirely within the insertion sleeve 19. Thus, the leading tip of the apparatus may be inserted into the anterior chamber 34 of the eye 32, as shown in FIG. 5*a*, through a small incision 505 (see FIG. 6).

Figure 5B:
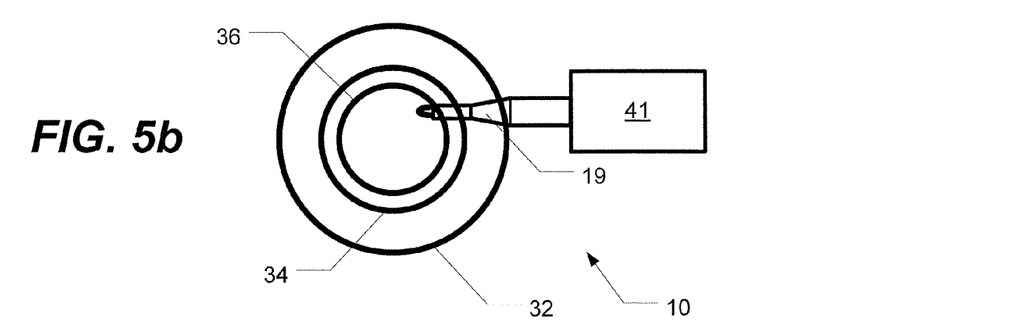
Figure 5C:
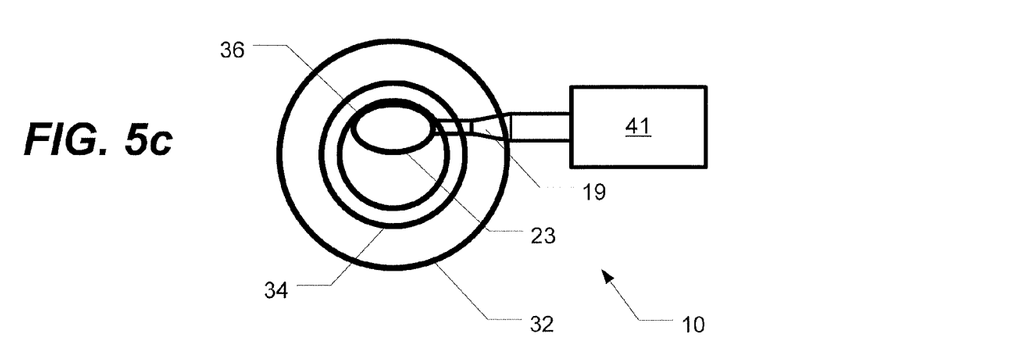
Figure 5D:
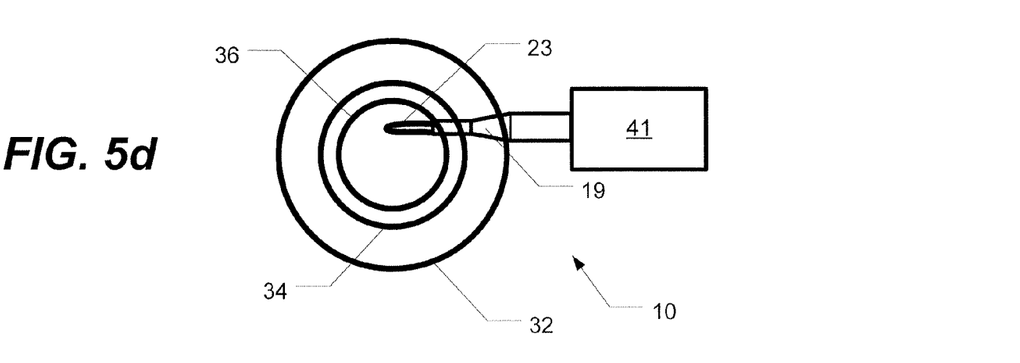

As shown in FIG. 5*b*, the insertion sleeve 19 and collapsed heating wire 14 may be pushed inside a posterior portion of the lens capsule 36 for posterior capsule polishing or near the anterior lens portion for anterior capsule polishing. The loop 23 of the heating wire 14 may then regain its pre-determined shape, as shown in FIG. 5*c*, and may then be positioned against the capsule 36. As noted above, the size and shape of the loop 23 may be designed to provide a contour that fits the capsule bag 36 so that sufficient contact may be established between the loop 23 and the contour 103 of the capsule bag 36. The heating wire 14 may then be energized, e.g., with a short pulse or series of pulses of current. As discussed above, this heating may destroy and/or remove LECs on the capsule after phacoemulsification. The heating wire 14 may then be retracted into the insertion sleeve 19, as shown in FIG. 5*d*, and then removed from the eye 32.

Figure 7A:
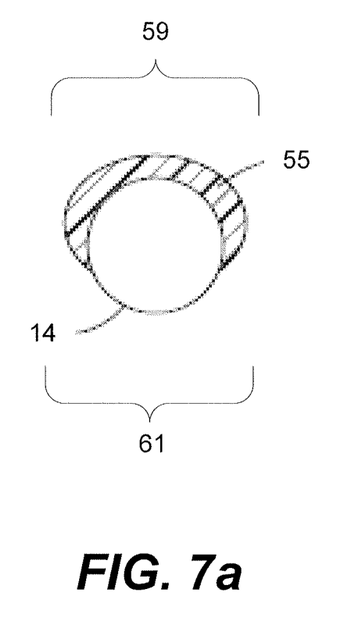
FIGS. 7a-b illustrate alternate configurations of the wire used in the capsule polishing device, according to various embodiments.
Figure 7B:
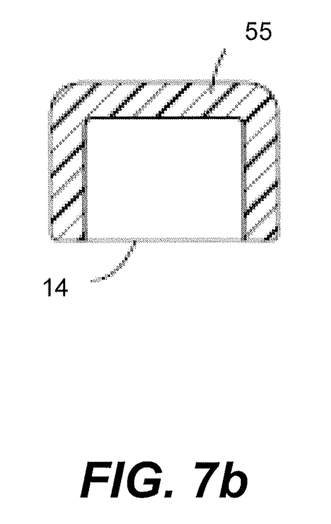

In some embodiments, to further reduce any potential collateral damage to tissue near the heating wire 14, a thermally insulating layer may be disposed on at least a top face 59 of the loop 23 formed by the resistive-heating wire 14, such that a bottom face 61, which may be disposed against the capsule 36 during the capsule polishing procedure, may be left bare. A cross-sectional view of one such embodiment is shown in FIG. 7*a*, which shows a cross-section of a round wire 14, partially surrounded with a thermally insulating layer 55. In some embodiments, the superelastic wire 14 may have a square or rectangular cross-section, as shown in FIG. 7*b*, in which case insulation 55 may be disposed on three sides of the wire 14. In either case, insulation 55 may be disposed on the wire 14 around all or substantially all of the loop 23 of the resistive-heating wire 14.

Figure 8:
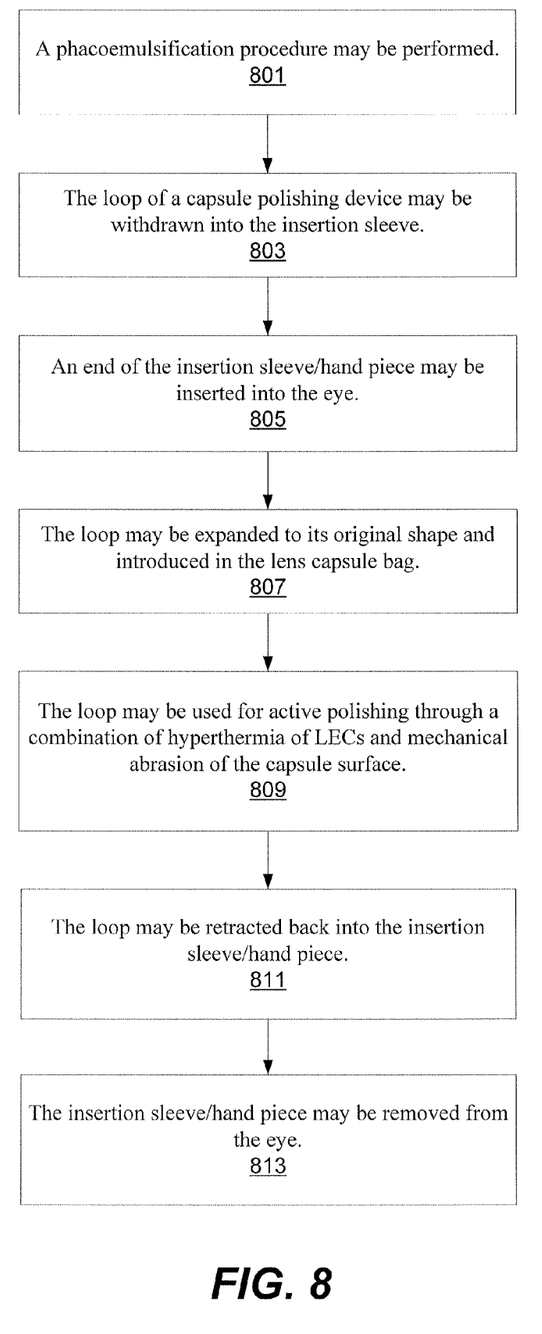
FIG. 8 illustrates a flowchart of a method for capsule polishing, according to an embodiment.

FIG. 8 illustrates a flowchart of an embodiment of a method for capsule polishing. The elements provided in the flowchart are illustrative only. Various provided elements may be omitted, additional elements may be added, and/or various elements may be performed in a different order than provided below.

At 801, a phacoemulsification procedure may be performed to remove a lens from the eye.

Figure 4B:
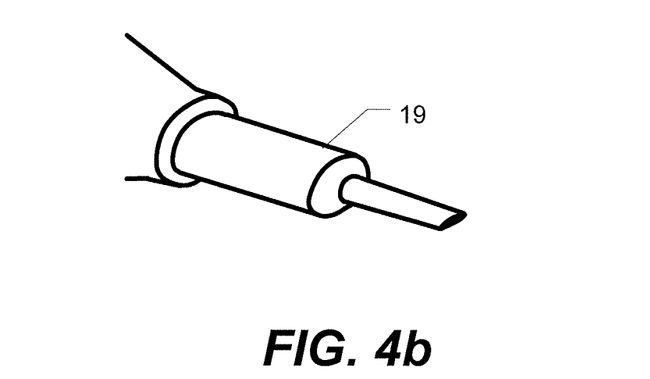

At 803, the loop 23 of a capsule polishing device 10 may be withdrawn into the insertion sleeve 19/hand piece 41. As seen in FIG. 2, in some embodiments, part of the wire 14 making up the loop 23 may be sticking out of the insertion sleeve 19 (e.g., to assist inserting the sleeve 19 through an incision in the eye). As seen in FIG. 4*b*, in some embodiments, the wire 14 may be enclosed in the insertion sleeve 19 (e.g., the insertion sleeve 19 may have a shape, such as a gradually pointed end, to assist in insertion).

At 805, an end of the insertion sleeve 19/hand piece 41 may be inserted into the eye (e.g., inserted into the anterior chamber through a small incision). In some embodiments, the end of the insertion sleeve 19 may be inserted in the same incision formed for insertion of a phacoemulsification handpiece tip (in some embodiments, a new incision may be made).

At 807, the loop 23 may be expanded to its original shape and introduced in the lens capsule bag 36. In some embodiments, the loop 23 may be pushed out of the insertion sleeve 19 or the insertion sleeve 19 may be pulled back to expose the loop 23 (e.g., using a lever 45 as seen in FIGS. 3*a-b*). Other extension methods are also possible (e.g., using a spring or solenoid).

At 809, the loop 23 may be used for active polishing through a combination of hyperthermia of LECs and mechanical abrasion of the capsule surface (see FIG. 1). The active polishing may destroy and/or remove LECs on the capsule after phacoemulsification without cutting through the lens capsule. In some embodiments, the surgeon may rub the loop 23 against the capsule surface as heat is being applied (e.g., through the application of current through the wire 23). In some embodiments, the surgeon may alternately rub the loop 23 and apply heat.

In some embodiments, energizing of the resistance-heating wire 14 may include a short pulse (e.g., 20 milliseconds) of electrical current, or a series of pulses (e.g., 1 millisecond each). In some embodiments, pulsed radio-frequency power may be used to reduce collateral thermal damage on the capsule and avoid electrochemical reaction at the gap 25. The frequency, waveform, voltage, pulse width, and duration of the radiofrequency power may be configured for removing LECs. Those skilled in the art will appreciate that the power settings (e.g., voltage, current, pulse width, number of pulses, etc.) may be established for a particular heating element configuration to remove LECs while minimizing collateral damage to portions of the capsule 36 surrounding the LECs. When determining the power settings for a particular heating wire 14 according to those described herein, those skilled in the art may consider that multiple working mechanisms (e.g., heat and abrasion) may contribute to the polishing of the capsule 36.

At 811, the loop 23 may be retracted back into the insertion sleeve 19/hand piece 41 (e.g., see FIG. 4*b*). In some embodiments, the loop 23 may be pulled into the insertion sleeve 19 or the insertion sleeve 19 may be pushed over the loop 23 (e.g., using a lever 45 as seen in FIGS. 3*a*-*b*). Other retraction methods are also possible (e.g., using a spring or solenoid).

At 813, the insertion sleeve 19/hand piece 41 may be removed from the eye 32.

Figure 9:
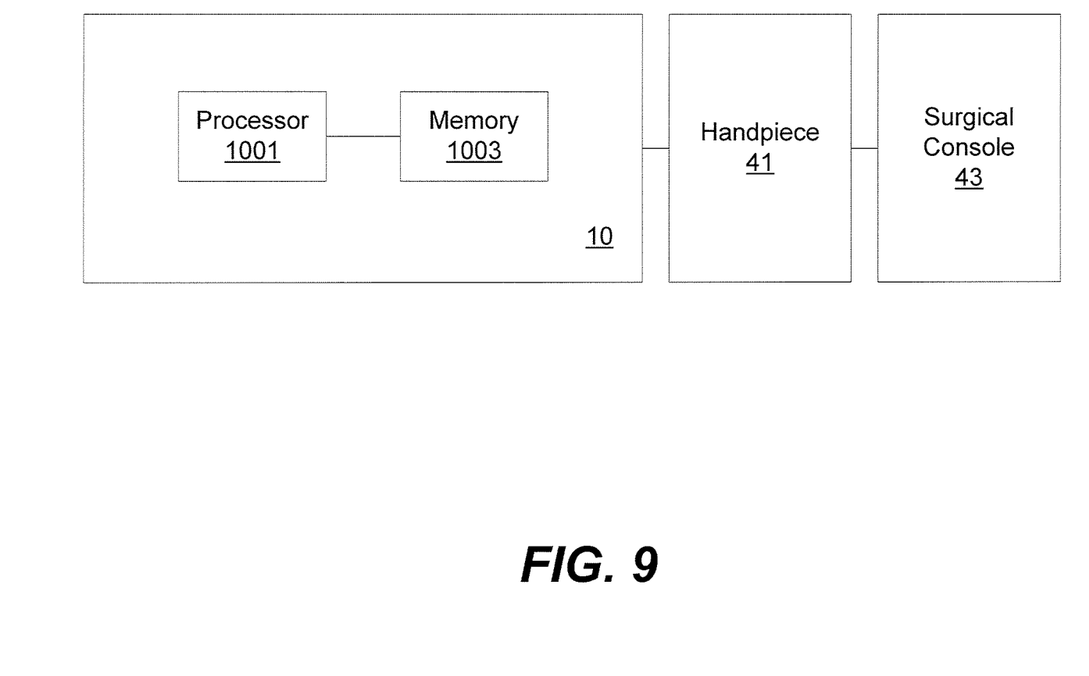
FIG. 9 illustrates a processor and memory for the capsule polishing device, according to an embodiment.

In some embodiments, the capsule polishing device 10 and/or a management system for the capsule polishing device 10 (e.g., handpiece 41 and/or console 43) may include one or more processors (e.g., processor 1001) and/or memory 1003 (e.g., see FIG. 9). The processor 1001 may include single processing devices or a plurality of processing devices. Such a processing device may be a microprocessor, controller (which may be a micro-controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. The memory 1003 coupled to and/or embedded in the processors 1001 may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processors 1001 implement one or more of its functions via a state machine, analog circuitry, digital circuitry, and/or logic circuitry, the memory 1003 storing the corresponding operational instructions may be embedded within, or external to, the circuitry comprising the state machine, analog circuitry, digital circuitry, and/or logic circuitry. The memory 1003 may store, and the processor 1001 may execute, operational instructions corresponding to at least some of the elements illustrated and described in association with the figures.

Various modifications may be made to the presented embodiments by a person of ordinary skill in the art. For example, although some of the embodiments are described above in connection with capsule polishing devices 10 it can also be used with other thermal surgical devices. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for capsule polishing, comprising:
    performing phacoemulsification to remove a lens from an eye;
    inserting a capsule polishing device comprising a bare wire resistive-heating element loop into the eye by ejecting the bare wire resistive-heating element loop in a collapsed loop configuration through an insertion sleeve into the eye whereby the bare wire resistive-heating element loop expands into an expanded loop configuration upon exiting the insertion sleeve, wherein the bare wire resistive-heating element loop comprises a bare electrically resistive, superelastic wire having first and second ends, the expanded loop configuration comprising the bare electrically resistive, superelastic wire formed in an open loop configuration having a gap between the first and second ends, wherein the first and second ends are adjacent to each other;
    electrically heating the bare wire resistive-heating element loop through application of radio frequency power to the loop, wherein electrically heating the bare wire resistive-heating element loop comprises providing a current to the first end of the loop and receiving the current back through the second end of the loop after the current has traveled around the loop;
    moving the heated bare wire resistive-heating element loop around a capsule surface of a lens capsule bag while applying heat and mechanical abrasion to destroy lens epithelial cells (LECs) without the heated bare wire resistive-heating element loop cutting through the lens capsule, wherein at least a side and end portion of the bare wire resistive-heating element loop are shaped to follow a contour of the lens capsule bag such that the heated bare wire resistive-heating element loop directly contacts the LECs during destruction of the LECs; and
    withdrawing the capsule polishing device from the eye by retracting the bare wire resistive-heating element loop into the insertion sleeve where the bare wire resistive-heating element loop collapses back into the collapsed loop configuration for withdrawal from the eye.

2. The method of claim 1, wherein a length of the bare wire resistive-heating element loop is approximately in a range of 4 to 5 mm.

3. The method of claim 1, wherein a width of the bare wire resistive-heating element loop is approximately in a range of 2.5 to 3.5 mm.

4. The method of claim 1, wherein electrically heating the bare wire resistive-heating element loop comprises heating the bare wire resistive element loop to a temperature of approximately 40 to 47 degrees Celsius to destroy LECs.

5. The method of claim 1, wherein the bare superelastic wire is made of a nickel titanium alloy.

6. The method of claim 1, wherein the resistive-heating element loop has a roughened surface and wherein applying mechanical abrasion comprises pressing the roughened surface against the capsule surface.

7. The method of claim 1, wherein the resistive-heating element loop has a surface with an applied abrasive and wherein applying mechanical abrasion comprises pressing the surface with an applied abrasive against the capsule surface.

* * * * *